United States Patent [19]
Piotrowski et al.

[11] Patent Number: 4,785,125
[45] Date of Patent: Nov. 15, 1988

[54] SYNTHESIS OF BIS(DICHLOROALUMINO)METHANE

[75] Inventors: Andrzej M. Piotrowski, Houston; Dennis B. Malpass, La Porte, both of Tex.

[73] Assignee: Texas Alkyls, Inc., Deer Park, Tex.

[21] Appl. No.: 116,847

[22] Filed: Nov. 5, 1987

[51] Int. Cl.$^4$ ............................................. C07F 5/06
[52] U.S. Cl. ................................................. 556/180
[58] Field of Search ........................................ 556/180

[56] References Cited

U.S. PATENT DOCUMENTS

| 3,509,189 | 4/1970 | Ort et al. | 556/180 |
| 3,509,190 | 4/1970 | Ort et al. | 556/180 |
| 3,577,450 | 5/1971 | Ort et al. | 556/180 |
| 3,700,710 | 10/1972 | Mottus et al. | 556/180 |

OTHER PUBLICATIONS

"J. Organomet. Chem.", (1973), pp. 47 to 52.

Primary Examiner—Paul F. Shaver
Attorney, Agent, or Firm—Richard P. Fennelly; Louis A. Morris

[57] ABSTRACT

A process for the synthesis of bis(dichloroalumino)methane, with a lessened danger of runaway reaction, entails the gradual addition of methylene bromide to a heated mixture of aluminum and methylene chloride. An aluminum alkyl activator is also advantageously present as a scavenger for moisture and oxygen to prevent undesired oligomer formation.

8 Claims, No Drawings

SYNTHESIS OF BIS(DICHLOROALUMINO)METHANE

BACKGROUND OF THE INVENTION

1. Field of the Invention

The present invention relates to a process for forming bis(dichloroalumino)methane.

2. Description of the Prior Art

Bis(dichloroalumino)methane is described in a variety of U.S. patents including U.S. Pat. Nos. 3,509,189, 3,509,190, 3,577,450 and 3,700,710. It is described as useful as a reagent in various types of syntheses. In copending U.S. Ser. No. 116,846, filed on even date herewith, entitled "Synthesis of Olefins from Ketones Using Bis(alkylchloroalumino)Methane", which is not prior art to the present invention, it is described as useful in the manufacture of bis(alkychloroalumino)methane reagents which can be used to convert ketones to olefins.

The synthesis of bis(dichloroalumino)methane is described in J. Organomet. Chem., 50(1973), 47–52, which required combining all of the reactants (aluminum, methylene chloride, and methylene bromide promoter) with initiation of the reaction by heating. Such a procedure works well when relatively small quantities of the compound are desired (e.g., a fraction of a mole, such as 1/6 mole). However, when larger amounts of reagent (e.g., aluminum reagent at 20 grams) are used, runaway reactions can occur. The present invention is directed to a modified procedure which avoids the problems of runaway reaction when such larger amounts of reagent e.g., aluminum reagent) are employed.

SUMMARY OF THE INVENTION

The present invention relates to an improved process for the preparation of bis(dichloroalumino)methane where a mixture of aluminum and methylene chloride are reacted with methylene bromide promoter which is gradually added thereto. Preferably, an aluminum alkyl is also used as an activator to avoid oligomeric by-product formation.

DETAILED DESCRIPTION OF THE INVENTION

The present process is practiced by first combining aluminum metal (preferably in the form of screened powder), methylene chloride, and, preferably, an aluminum alkyl such as triethyl aluminum (TEAL). The aluminum alkyl functions as a moisture and oxygen scavenger thereby achieving a desired activation of the entire reaction to avoid the oligomeric by-product formation noted in U.S. Pat. No. 3,509,189. The molar ratio of aluminum to methylene chloride can range from about 1:4 to about 1:10. The amount of aluminum alkyl used can range from about 0.01 molar to about 0.25 molar, based on the moles of aluminum used.

The foregoing admixture is then heated (e.g., to about 40°–47° C.) and the methylene bromide promoter is gradually added, e.g., at a rate of from about 6 ml/hour/mole Al to about 12 ml/hour/mole Al, to achieve the desired reaction and production of bis(dichloroalumino)methane.

The desired product, bis(dichloroalumino)methane, can be suspended in a suitable solvent, such as toluene, and can be treated with tetrahydrofuran (e.g., two equivalents thereof) to form the soluble complex bis(dichloroalumino) methane.2 tetrahydrofuran, if desired.

The present invention is further illustrated by the Examples which follow.

EXAMPLE 1

Aluminum powder (Alcoa 120 brand) was screened and a $-90/+150$ mesh function was collected. It was then ball milled in Isopar ® paraffinic solvent for 72 hours in the presence of a small amount of triethyl aluminum (TEAL) (2 milliliters). Aluminum flakes were then washed with isopentane and dried in a stream of nitrogen. The fraction, $12/+35$ mesh, was used in the syntheses of bis(dichloroalumino)methane (BDAM). Aluminum flakes (19.0 grams) prepared as described above were placed in a 3OO-milliliter flask equipped with reflux condenser, nitrogen inlet and thermocouple. Two milliliters of TEAL and 200 milliliters of dry methylene chloride were added. The reaction mixture was warmed by placing in an oil bath (52° C.). After about 15 minutes of stirring, 2 milliliters of $CH_2Br_2$ were added. After ½ hour stirring, under mild reflux, a more vigorous reflux was noticed, and the aluminum flakes started to darken. Six more 2-milliliter portions of $CH_2Br_2$ were added over a period of 90minutes. After the addition of $CH_2Br_2$ was completed, the reaction mixture was refluxed for ½ hour. At this point, almost all the aluminum had reacted and only a small amount of fine black powder was left. The reaction mixture was filtered through diatomaceous earth (Celite brand) and the solvent was evaporated under vacuum. A total of 55 grams of a tan solid was obtained. See Table I for analytical data.

EXAMPLES 2–4

Three more syntheses were conducted using the quantities of reagents described in Table I. The yields and analytical data for these syntheses are also listed in Table I.

TABLE I

Products Yields and Analytical data

| Exp. No. | Quantities of Reagents Used | | |
|---|---|---|---|
| | Al (g) | $CH_2Cl_2$ (ml) | $CH_2Br_2$ (ml) |
| 1 | 14 | 200 | 14 |
| 2 | 20 | 260 | 16 |
| 3 | 14 | 250 | 12 |
| 4 | 14 | 200 | 14 |

| Exp. No. | Activator | | Yield* % | Product analysis Weight %*** | |
|---|---|---|---|---|---|
| | Compound | Quantity | | Al | Cl |
| 1 | Et$_3$Al | 2.0 | 88 | 23.1 | 55.4 |
| 2 | Et$_3$Al | 3.0 | 85 | 22.2 | 54.9 |
| 3 | Me$_3$Al | 1.0 | 83** | 24.1 | 61.8 |
| 4 | Me$_3$Al | 1.5 | 86 | 22.1 | 56.7 |

*Yield = $\frac{\text{(grams product) (weight \% Al)}}{\text{grams Al used + grams Al in activator}}$

**Product washed with 200 milliliters of fresh methylene chloride.

***Aluminum analyses were done according to Crompton T. R., "Analysis of Organoaluminum and Organozinc Compounds", Pergamon, London, 1968, p. 27, whereas chlorine analyses were done according to Martin, A. J., 1958, 30, 233.

The foregoing should be taken as merely illustrative of the present invention and should not be construed in a limiting sense. The scope of protection is set forth in the claims which follow.

We claim:

1. A process for the production of bis(dichloroalumino)methane which comprises the gradual addition of methylene bromide to a mixture comprising methylene chloride and aluminum.

2. A process as claimed in claim 1 wherein an aluminum alkyl activator is also present.

3. A process as claimed in claim 1 wherein the addition takes place at a temperature of from about 40° C. to about 47° C.

4. A process as claimed in claim 1 wherein the aluminum is in powder form.

5. A process as claimed in claim 3 wherein an aluminum alkyl activator is also present.

6. A process as claimed in claim 1 wherein the methylene chloride and aluminum are in a molar ratio of from about 4:1 to about 10:1.

7. A process as claimed in claim 6 wherein an aluminum alkyl activator is also present at from about 0.01 molar to about 0.25 molar based on the molar amount of aluminum used.

8. A process as claimed in claim 7 wherein the aluminum alkyl activator is triethyl aluminum.

* * * * *